United States Patent
Hamamoto et al.

(10) Patent No.: US 6,495,045 B2
(45) Date of Patent: Dec. 17, 2002

(54) SOLID SUBSTANCE REMOVING DEVICE

(75) Inventors: Kei Hamamoto, Himeji (JP); Yukihiro Matsumoto, Kobe (JP); Sei Nakahara, Himeji (JP); Naoto Kasaya, Himeji (JP); Masakatsu Mori, Hyogo (JP)

(73) Assignee: Nippon Shokubai Co., Ltd. (JP)

( * ) Notice: Subject to any disclaimer, the term of this patent is extended or adjusted under 35 U.S.C. 154(b) by 70 days.

(21) Appl. No.: 09/880,395

(22) Filed: Jun. 13, 2001

(65) Prior Publication Data

US 2002/0008064 A1 Jan. 24, 2002

(30) Foreign Application Priority Data

Jun. 19, 2000 (JP) .......................... 2000-183550

(51) Int. Cl.$^7$ .......................... B01D 11/00; B01D 27/00; A61L 2/00
(52) U.S. Cl. .......................... 210/634; 210/634; 210/435; 210/767; 210/806; 209/422; 209/554; 422/292; 422/311; 422/312
(58) Field of Search .......................... 562/600; 560/218; 203/47; 202/152, 158; 210/634, 435, 767, 806; 209/422, 554; 422/292, 311, 312

(56) References Cited

U.S. PATENT DOCUMENTS 5,637,222 A * 6/1997 Herbst et al.
5,892,103 A * 4/1999 Sogabe et al.

FOREIGN PATENT DOCUMENTS

JP             A 823941           8/1996

* cited by examiner

Primary Examiner—J. Parsa
Assistant Examiner—Farhad Forohar
(74) Attorney, Agent, or Firm—Mathews, Collins, Shepherd & McKay, P.A.

(57) ABSTRACT

A solid substance removing device comprising a body provided with a fluid inlet pipe and a fluid outlet pipe and a filtering part disposed between the fluid inlet pipe and the fluid outlet pipe inside said body, the filtering part having (a) a thickness in the range of 5–500 mm, (b) a percentage of voids in the range of 60–99.5 vol. %, and (c) a contact surface area in the range of 100–2000 m$^2$/m$^3$. Owing to the construction described above, it is made possible to facilitate removal of the solid substance and, at the same time, prevent new generation of a polymer during the production of an easily polymerizing substance.

6 Claims, 4 Drawing Sheets

SOLID SUBSTANCE REMOVING DEVICE

BACKGROUND OF THE INVENTION

1. Field of the Invention

This invention relates to a solid substance removing device, a purifying device, a method for the removal of solid substance, and a method for the production of (meth)acrylic acid.

2. Description of Related Art

Such easily polymerizing compounds as acrylic acid and methacrylic acid are raw materials for commercial production and are chemical substances which are produced in a large amount at a plant of a large scale. In the case of (meth)acrylic acid, for example, the easily polymerizing compound is produced by the reaction of catalytic gas phase oxidation of propylene, isobutylene, t-butanol, methyl-t-butyl ether, or acrolein. The reaction gas obtained by the reaction of catalytic gas phase oxidation contains (meth)acrylic acid, the target product, as mixed with other by-products. For example, this reaction generates mainly non-condensable gases, namely unreacted propylene and isobutylene; low-boiling compounds having lower boiling points than acrylic acid, namely steam and unreacted acrolein, formaldehyde produced by a side reaction, and impurities such as acetic acid; and high-boiling compounds having higher boiling points than acrylic acid, namely maleic anhydride, furfural, benzaldehyde, benzoic acid, and acrylic acid dimer. For the purpose of purifying this reaction gas thereby obtaining the target product, therefore, the reaction gas is washed with a counter flow water or heavy solvent thereby extracting the gas and subsequently supplying the extracted gas to a purifying column and completing the target product through various means such as distillation, stripping, absorption, and purification generally.

The easily polymerizing substances, however, have such a chemical property that they are possibly compelled by the heating conditions or the pressure conditions prevailing during the process of production to form polymers and gelling matter under the influence of impurities and by-products.

When such solid substance impurities are not extracted as a target product but are suffered to stagnate in the fluid under treatment or adhere thereto and deposit thereon, they possibly entail further adhesion of other impurities thereto. The solid substance which stagnates over, adheres to, or deposits on the interior of a purifying column clog pipes and devices attached to the purifying column. Otherwise, the solid substance partly mingles into the target product and causes a degradation of the quality of the product. For the purpose of stably operating the purifying column by maintaining the quality of treatment in the column, therefore, it becomes necessary to operate the periodic observation of opening the purifying column and removing the polymer adhering to the inner wall of the column. This extra work greatly consumes time and labor and profusely degrades the productivity.

As a means for solving these problems, a method which consists in attaching a filtering device to a strainer or a filter of the purifying column has been conceived. Such a known removing device, however, is incapable of thoroughly removing a solid substance impurity such as precipitate or polymer. When the solid substance impurity which has escaped the removal adheres to the interior of a device of the subsequent step, as a result the process can not operate sequentially because the removing device has no alternative but to cease operating. For the purpose of enabling the purifying column to operate stably by maintaining the quality of the fluid under treatment therein, it is necessary to remove periodically the polymer adhering to the inner wall of the purifying column with an enormous cost of time and labor and at the sacrifice of productivity of the target product, contrary to the object of mass production.

The official gazette of JP-A-08-239341, for example, discloses a method for separating oligomer, etc. by extracting from a purifying column the reflux liquid descending the interior of the column from at least one point of the column and separating the (meth)acrylic acid of the oligomer and/or the polymer present in the extracted reflux liquid. Specifically, as concrete examples of the means for separating the (meth)acrylic acid of the oligomer and/or the polymer from the refluxed liquid mentioned above, methods which resort to ultrafiltration, and chromatography and a method which utilizes a temporary retaining tank enabling the fluid of a distilling device, for example, to remain in the boiling state are enumerated.

When the purifying column is started by the conventional method and the object for purification is such an easily polymerizing substance as (meth)acrylic acid, the places which are liable to generate a polymer include the bottom part of the wall of the purifying column, the condenser attached to the purifying column, and the reboiler requiring temperature elevation, for example. When a strainer is attached to the extraction pump connected to the bottom of the column, therefore, the pump is not only clogged by the adhesion of the polymer but also stopped by the occurrence of cavitation due to adhesion of the polymer to the interior of the strainer. Thus, the safe operation of the purifying column is possibly spoiled.

There is also a time when the stagnation of a liquid generates a polymer, gradually accumulates as a core of the polymer, and induces further polymerization and clogging.

Further, the adhesion of the polymer to the strainer or the clogging of the strainer with the polymer necessitates a cleaning operation. The chemical stimulation by the raw material for the reaction, the reaction product, and the by-products and the physical hindrances due to the adhesion of a polymer inflict a spiritual displeasure on the worker engaged in the cleaning operation and bring about an alarming influence on his health. Further, the cleaning work entails the problem of jeopardizing his safety as the n of an organic solvent to be used for distillation. Further, the manual removal of the waste of the washing work for disposal is generally difficult, based on the size of the device used for the washing and removing work and the size of the purifying column itself as contributory factors.

SUMMARY OF THE INVENTION

The present inventor, after pursuing an elaborate study on the solid substance which is generated in a purifying column handling an easily polymerizing substance, has found that the solid substance can be easily removed by the use of a solid substance removing device attached to a specific filtering part and further occurrence of a polymer can be prevented by having the device incorporated in the process for the production of an easily polymerizing substance. This invention has been perfected as a result. The tasks mentioned above are accomplished by the following items (1)–(4).

(1) A solid substance removing device comprising a body provided with a fluid inlet pipe and a fluid outlet pipe and a filtering part disposed inside the body between the fluid inlet pipe and the fluid outlet pipe inside the body, the filtering part having (a) a thickness in the range of 5–500 mm, (b) a percentage of voids in the range of 60–99.5 vol. %, and (c) a contact surface area in the range of 100–2000 m$^2$/m$^3$.

(2) A purifying apparatus which has disposed in a purifying column handling an easily polymerizing substance and provided with a solid substance removing device thereon set forth in (1) above.

(3) A method for the removal of a solid substance, characterized by introducing the bottom liquid of a purifying column handling an easily polymerizing substance into a solid substance removing device set forth in (1) above and circulating at least part of the fluid discharged through the fluid outlet pipe of the device to the purifying column.

(4) A method for the production of (meth)acrylic acid or an ester thereof by the use of a method set forth in (3) above.

According to this invention, a solid substance removing device which permits removal of solid substance in a purifying column particularly handling an easily polymerizing substance, prevents new generation of a polymer, and causes a polymer to transfer to the next step only sparingly is provided. The solid substance removing device of this invention, when disposed in a purifying column, is enabled to remove the polymer in the purifying column. By using the solid substance removing device and the purifying apparatus according to this invention, it is made possible to produce an easily polymerizing substance very stably for a long time.

BRIEF DESCRIPTION OF THE INVENTION

DETAILED DESCRIPTION OF THE PREFERRED EMBODIMENTS

The first aspect of this invention consists in a solid substance removing device comprising a body provided with a fluid inlet pipe and a fluid outlet pipe and a filtering part disposed between the fluid inlet pipe and the fluid outlet pipe inside the body, the filtering part having (a) a thickness in the range of 5–500 mm, (b) a percentage of voids in the range of 60–99.5vol. %, and (c) a contact surface area in the range of 100–2000 m$^2$/m$^3$.

Figure 1:
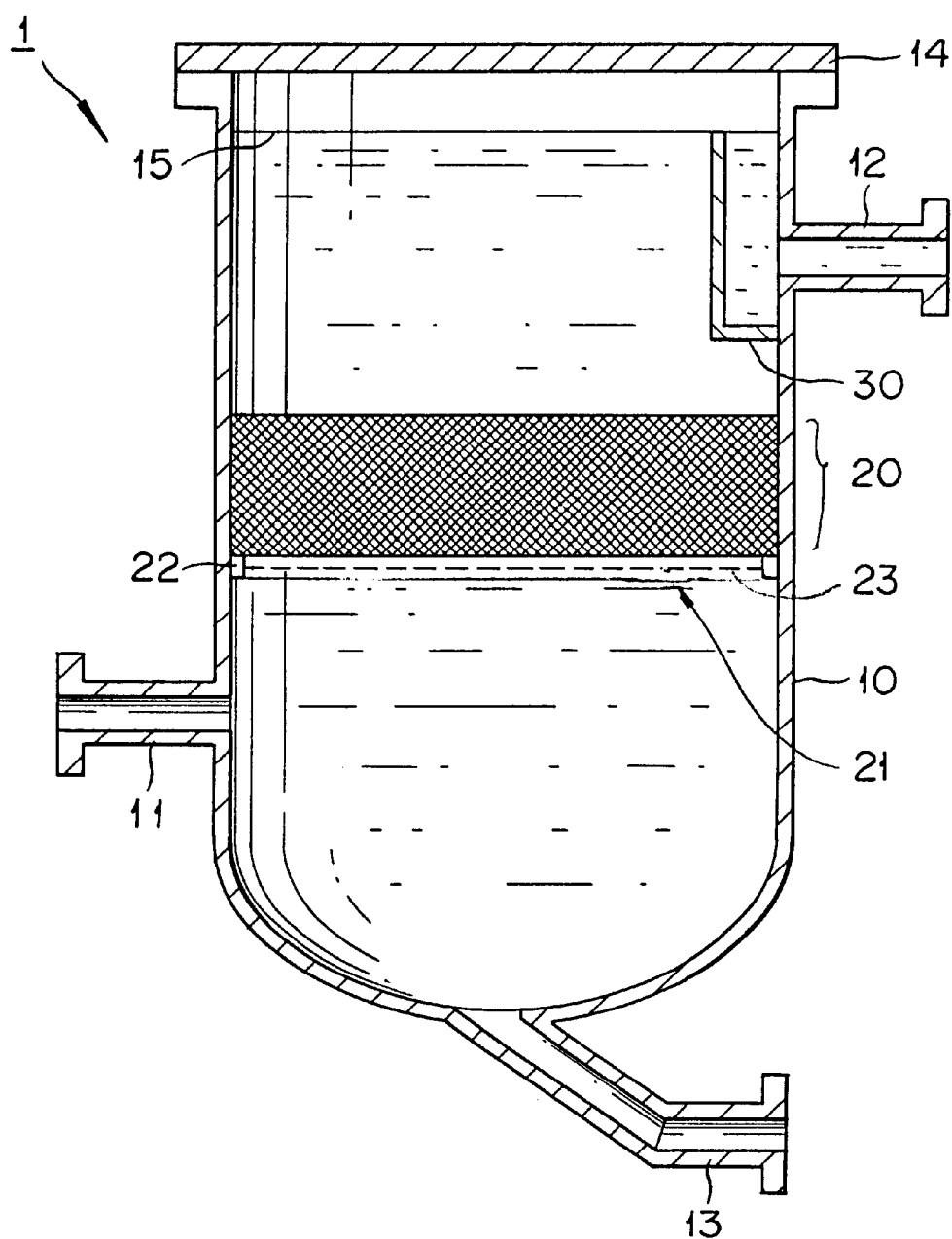
FIG. 1 is a longitudinal cross section of the solid substance removing device of this invention.

Now, a preferred mode of embodying the solid substance removing device of this invention will be described below with the aid of FIG. 1. With reference to FIG. 1, 1 represents a solid substance removing device, 10 a body, 11 a fluid inlet pipe, 12 a fluid outlet pipe, 13 a drain, 14 a lid part, 15 a liquid level or liquid surface, 20 a filtering part, 21 a fluid inlet for the filtering part, 22 a support ring, 23 a grid, and 30 a baffle.

The fluid is introduced into the solid substance removing device (1) via the fluid inlet pipe (11) disposed in the lower part of the solid substance removing device (1). The fluid is advanced toward the filtering part (20) disposed in the upper part of the solid substance removing device (1) and separated into the solid substance and the fluid.

The body (10) does not need to be particularly discriminated on account of the shape thereof. It may be in a tubular shape, an angular shape, or other properly selected shape to suit the occasion. Particularly, the body is preferred to be in a tubular shape.

The fluid inlet pipe (11) is only required to exist below the filtering part (20). The position thereof does not need to be particularly restricted. The relevant pipes may be so laid as to oppose the opening part of the liquid inlet pipe (11) to the fluid inlet (21) of the filtering part (20). The diameter of the fluid inlet pipe (11) does not need to be particularly limited. When the body (10) is in a tubular shape, the diameter of the fluid inlet (21) is properly in the range of 0.01–1 times, more preferably in the range of 0.02–0.5 times, and particularly preferably in the range of 0.05–0.2 times, the diameter of the body (10). If the diameter falls short of 0.01 times the diameter of the body (10), the shortage will be at a disadvantage in unduly decreasing the amount of the fluid to be treated per unit time. An addition to the amount of the fluid to be supplied per unit time will be at a disadvantage in inducing the fluid to produce a turbulent flow. Conversely, if the diameter exceeds 1 times the diameter of the body (10), the excess will be at a disadvantage in rendering the installing work of pipes difficult.

The filtering part (20) may be formed by laminating a plurality of wire gauzes. It may be otherwise formed by interposing between two opposed wire gauzes what is packed with metal pieces cut in a linear, sheet, or other indeterminate shape or metal cubes in a triangular, quadrangular or other polygonal, spherical, or indeterminate shape. This invention prefers the filtering part (20) to be formed by laminating wire gauzes. Though the method for laminating wire gauzes do not need to be particularly discriminated. As concrete examples of the method available for the purpose of the lamination, a method which comprises laminating wire gauzes as arranged in a sheet direction, a method which comprises laminating wire gauzes as arranged in a vertical direction, a method which comprises spiraling wire gauzes and laminating the spiral wire gauzes as arranged in a planar direction, and a method which comprises spiraling wire gauzes and laminating the spiral wire gauzes as arranged in a vertical direction may be cited. By using the wire gauzes in the laminated state, it is made possible to facilitate the production of the filtering part and enable the filtering part to excel in the ability to remove solid substance. When such a laminated wire gauze is used, this mass is preferred to result from laminating wire gauzes in such a manner that their meshes may be lined up. The reason for this preference of this mode of lamination is that the ability of the filtering part (20) to remove the solid substance is improved. Specifically, by this mode of lamination, it is made possible to form innumerable empty spaces regularly in the interior of the filtering part, and the filtering area throughout the entire area of the laminated mass uniformly, render infallible the function of dispersing the solid substance to the filtering part, and moreover make effective use of the entire interior of the filtering part.

The member for forming the filtering part (20) of this construction does not need to be particularly discriminated. It is, however, preferred to be an austenitic stainless steel, austenitic-ferritic stainless steel, or ferritic stainless steel.

The reason for this preference is that the material avoids reacting with the target product, shuns alteration of the easily polymerizing substance, and nevertheless excels in durability as in the form of resistance to corrosion.

Then, the method for fitting the body (10) to the filtering part (20) is preferred to use an attachment easy of handling and capable of retaining these two parts in a coupled state. For example, the coupling may be attained by fitting the support ring (22) to the body (10), disposing the grid (23) on the support ring (22), and setting the filtering part (20) up on the support ring (22). Optionally, the grid (23) is disposed further on the filtering part (20) and fixed thereon firmly. The filtering part (20) is also fixed by fixing the support ring (22) and the grid (23) with bolts and nuts. The filtering part (20) and the grid (23) may be further fixed with bolts and nuts. As respects the method of this fixing, the bolts and nuts are no sole means available and wires may be used instead.

The thickness of the filtering part (20) in the direction from the fluid inlet pipe (11) to the fluid outlet pipe (12) is properly in the range of 5–500 mm, more preferably in the range of 10–450 mm, and particularly preferably in the range of 50–400 mm. If this thickness falls short of 5 mm, the shortage will be at a disadvantage in unduly decreasing the filtering area, suffering the filtering part to be instantly filled to capacity with such solid substance as polymer and impurity, and requiring the filtering part to be cleaned. Conversely, if the thickness exceeds 500 mm, the excess, though capable of adding to the filtering area, will be nevertheless at a disadvantage in increasing the pressure loss in the removing device, enlarging the apparatus, and increasing the cost of equipment.

In this invention, the percentage of voids of the filtering part (20) is in the range of 60–99.5 vol. %, more preferably in the range of 70–99.3 vol. %, and particularly preferably in the range of 80–99 vol. %.

The term "percentage of voids" as used herein means the volume percentage of the empty space less the volume of the packing relative to the total volume of the filtering part (20). This percentage of voids, when explained on the assumption that the filtering part (20) is the mass of lamination of a plurality of wire gauzes, may be expressed by the following formula.

Figure 2:
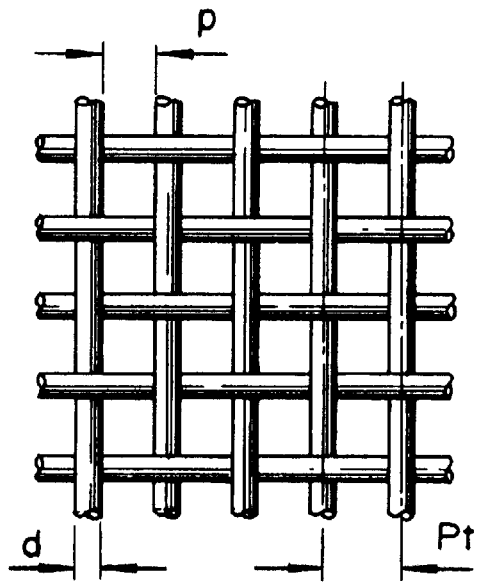
FIG. 2 is a model diagram of a wire gauze for forming a filtering part.

Percentage of voids, $\epsilon(\%) = [1 - \{\text{volume of packing}/(\text{empty space of the filtering part} + \text{volume of packing})\}] \times 100$ To explain the term more specifically on the assumption that the filtering part (20) is a laminated wire gauze illustrated in FIG. 2, let d stand for the diameter (mm) of a wire gauze, $P_t$ for the pitch (mm) of arrangement of the wire gauze, ρ for the mesh (mm), N for the number of wire gauzes per 1 mm of thickness, V for the total of the volume (m³) of the wire gauzes and the volume of the empty space part, and $V_1$ for the volume (m³) of the wire gauzes, and the percentage of voids ε (%) will be expressed by the following equation.

Percentage of voids $\epsilon(\%) = [1 - V_1/V] \times 100 = [1 - \{1 - (P_t - d)^2/P_t^2\} \times d \times N] \times 100$ If the percentage of voids falls short of 60 vol. %, the shortage will be at a disadvantage in being the high density in the removing device and degrading the ability of the filtering part to remove the solid substance. It also has the possibility of deforming the filtering device due to the expansion of the polymer during the course of washing, increasing the frequency of use, and at the same time considerably degrading the efficiency of washing. Conversely, if the percentage of voids exceeds 99.5 vol. %, the excess will be at a disadvantage in being the low density in the removing device and consequently degrading the ability of the filtering part to remove the solid substance. It also has the possibility of suffering the polymer to be transferred into the subsequent step. The adhesion of the polymer has the possibility of inducing the filtering part to generate cavitation and consequently inflicting damage to the relevant devices.

The contact surface area of the filtering part (20) is in the range of 100–2000 m²/m³, more preferably in the range of 200–1800 m²/m³, and particularly preferably in the range of 300–1500 m²/m³. The term "contact surface area" as used herein means the total surface area of the packing filling up the filtering part (20) relative to the total volume of the filtering part (20). To explain this term with the aid of FIG. 2, the contact surface area, b, (m²/m³) is expressed as $4/d \times (1 - \epsilon/100) \times 10^3$.

If the contact surface area falls short of 100 m²/m³, the shortage will have the possibility of affording insufficient contact with the fluid, degrading the efficiency of the removal of the solid substance, exerting an adverse effect on the subsequent step, and inducing generation of cavitation and consequently inflicting damage to the relevant devices. Conversely, if the contact surface area exceeds 2000 m²/m³, the excess will be at a disadvantage in unduly decreasing the diameter of the wires forming the wire gauzes where the packing is the laminated wire gauze and possibly degrading the strength of the filtering part or rendering the production of the filtering part difficult. Consequently, the filtering part will inevitably require huge strength for its retention.

Where the member forming the filtering part (20) is the laminated mass of wire gauzes, the diameter of the wires in the wire gauzes is properly in the range of 0.01–3 mm, preferably in the range of 0.02–2 mm. The number, N, of the wire gauzes per 1 mm of thickness, though generally determined by the method of weaving the gauze, is properly in the range of 0.1–10/mm, more preferably in the range of 0.2–5/mm.

Figure 3:
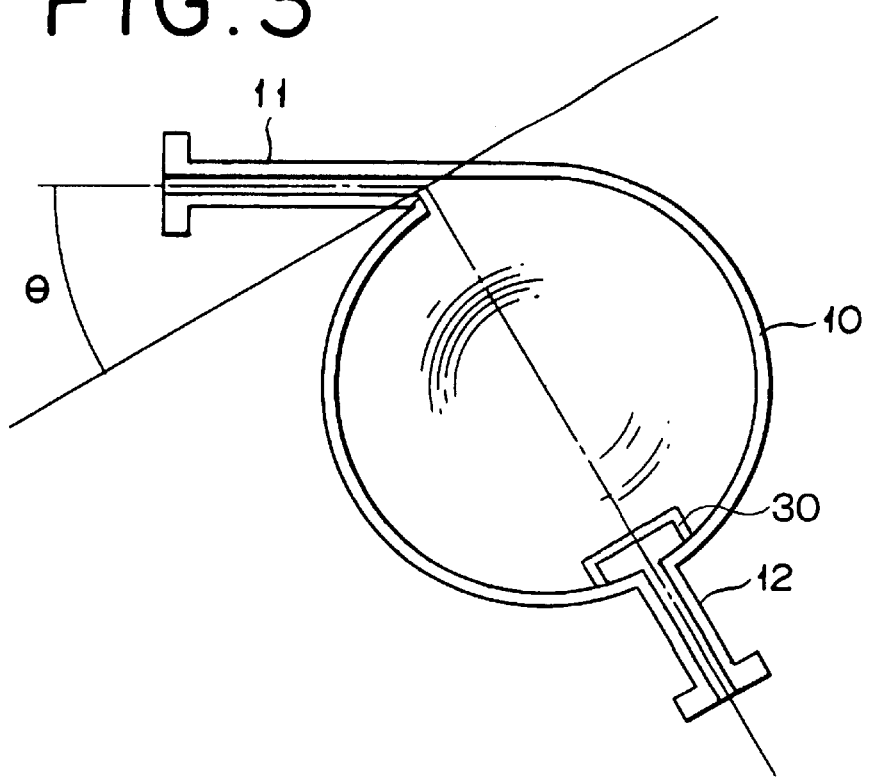
FIG. 3 is a horizontal cross section of the solid substance removing device shown in FIG. 1, i.e. a schematic diagram showing the fitting angle (θ) of a fluid inlet pipe (11) relative to the tangential line of a body (10).

The fluid has the solid substance therein separated with the filtering part (20). In this case, the fluid is preferred to pass uniformly the whole of the filtering part (20) because the uniform passage prevents the fluid from forming a deflective current, effects uniform removal of the solid substance, and improve the ability of the filtering part to remove the solid substance. For the purpose of enabling the fluid to pass the filtering part (20) uniformly, the fluid is caused in the body (10) to produce a swirling current. To be specific, the fluid inlet pipe (11) is provided therein guide vanes, the fluid inlet pipe (11) is provided therein a baffle adapted to produce a swirling current, or, where the body (10) is in a tubular shape as illustrated in FIG. 3, the fluid inlet pipe (11) is disposed at a position in the range of 30–60° from the tangential line of the body of the solid substance removing device (1). In this invention, particularly the position to attach the fluid inlet pipe (11) is properly in the range of 30–60° and more preferably in the range of 35–55°. By adjusting such range, no interior part needs to be relied on to generate the swirling current, the otherwise possible occurrence of a new polymer due to the contact with such interior part can be precluded and the generation of a swirling current and the production of the device can be both facilitated. If the angle of the position falls short of 30°, the shortage will be at a disadvantage in suffering the fluid to collide vigorously against the inner wall of the body (10) and give rise to an agitating current, rendering uniform filtration difficult, and allowing no easy welding between the body (10) and the fluid inlet pipe (11). Conversely, if the angle exceeds 60°, the excess will be at a disadvantage in increasing the amount of the fluid passing the center of the solid substance removing device (1) and rendering uniform filtration difficult.

Subsequently, the fluid which has the solid substance separated with the filtrating part (2) is advanced toward the fluid outlet pipe (12) and discharged out of the solid removing device (1). The fluid emanating from the device possibly entrain a gas component. If the gas component in its unreacted form is left advancing through the fluid outlet pipe (12) and reaching the exterior of the solid substance removing device (1), the fluid will possibly generate a new polymer by being mixed with the gas component. If the fluid incorporates the gas component therein, the resultant mixture will possibly generate cavitation and inflict damage to the relevant devices. Since the gas component generally collects in the upper part of the solid substance removing device (1), the filtering part (20) is preferred to be provided with a gas discharge preventing mechanism which allows only the fluid to be discharged through the fluid outlet pipe (12).

Figure 4:
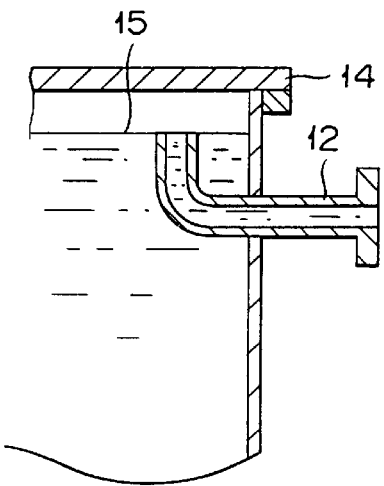
FIG. 4 is a partial cross section of the solid substance removing device depicting one mode of a gas discharge preventing mechanism for the solid substance removing device of this invention.

As concrete examples of this mechanism, the baffle (30) which is disposed in the proximity of the connecting part of the fluid outlet pipe (12) inside the solid removing device (1) as illustrated in FIG. 1 and the fluid outlet pipe (12) which is thrust into the solid substance removing device (1) and which has the terminal part thereof bent in the direction of the liquid surface (15) as illustrated in FIG. 4 may be cited. By fitting the liquid outlet pipe (12) at a position not higher than the liquid level (15), it is made possible to discharge the fluid alone always through the fluid outlet pipe (12) and prevent the mixture of the fluid with the gas component and prevent the generation of a new polymer.

Incidentally, the diameter of the fluid outlet pipe (12), similarly to that of the outlet inlet pipe (11), does not need to be particularly discriminated. This diameter may be selected in consideration of the amount of discharge per unit time and the linear velocity of the fluid so as to confirm to the diameter of the fluid inlet pipe (11).

The solid substance removing device (1) of this invention may be provided therein with a pump as a means for passing the fluid. The efficiency with which the removal of the solid substance is attained increases in accordance as the amount of the fluid to be circulated is increased. This amount of the fluid to be circulated is properly set in consideration of the amount of the solid substance impurity in the fluid under treatment and the quantity of the solid substance impurity. The solid substance removing device (1) may be provided in the bottom part thereof with the drain (13).

The solid substance removing device (1) of this invention furnished in the upper part of the body (10) with the lid part (14). When the filtering part (20) has adsorbed the solid substance, the lid part (14) may be removed to clean the interior of the device.

Incidentally, the material for forming the body (10), the fluid inlet pipe (11), the fluid outlet pipe (12), the drain (13), the lid part (14), the support ring (22), and the grid (23) is preferred to be an austenitic stainless steel, an austenitic-ferritic stainless steel, or a ferritic stainless steel. This metal avoids reacting with the target product, shuns alteration of the easily polymerizing substance, and nevertheless excels in durability as in the form of resistance to corrosion.

Further, the inner wall surface of the body (10) is preferred to have a surface roughness, Ry, of not higher than 12.5 as specified in JIS (Japanese Industrial Standards) B0601 (-1994) because the rough surface permits no stagnation of the easily polymerizing substance on the inner wall and prevents the easily polymerizing substance from generating a polymer or inducing adhesion of the polymer. As concrete examples of the method for such a surface treatment, electropolishing, chemical polishing, and buffing may be cited. Further adoption of a method for producing mirror finish proves more advantageous.

The particle diameter of the solid substance which can be removed with the solid substance separating device of this invention is not less than 0.1 $\mu$m and more preferably in the range of 0.1–1000 $\mu$m.

The second aspect of this invention consists in a purifying apparatus which has disposed in a purifying column handling an easily polymerizing substance a solid substance removing device thereon set forth above. The third aspect of this invention consists in a method for the removal of solid substance, characterized by introducing the bottom liquid of a purifying column handing an easily polymerizing substance into the solid substance removing device mentioned above and, at the same time, circulating at least part of the fluid discharged through said fluid outlet pipe of said device to the purifying column.

The solid substance removing device of this invention excels in the ability to remove the solid substance contained in the fluid. When this device is furnished with a swirling current generating mechanism and a gas discharge preventing mechanism, it excels in respect that this device permits particularly uniform removal of the solid substance and shuns new generation of a polymer. Thus, when the solid substance removing device is attached to the purifying column handling a particularly easily polymerizing substance, an unusually excellent purifying apparatus for an easily polymerizing substance is derived without entailing adulteration with a polymer at the subsequent step.

The easily polymerizing substance includes an easily polymerizing substance-containing solution. This substance, on account of its chemical property, is liable to generate a polymer by virtue of temperature, pressure, contact, stirring, etc. As concrete examples of the easily polymerizing substance which forms the target for application, carboxylic acids such as acrylic acid, methacrylic acid, fumaric acid, and maleic acid which possess an unsaturated double bond and esters thereof may be cited. As concrete examples of the acrylic ester, methyl acrylate, ethyl acrylate, butyl acrylate, and 2-ethylhexyl acrylate may be cited. As concrete examples of the methacrylic ester which forms the target for application, methyl methacrylate, ethyl methacrylate, and butyl methacrylate may be cited.

The hydroxyl group-containing compound which forms an ester with the aforementioned carboxylic acid possessing an unsaturated double bond is preferred to be a lower aliphatic alcohol or a lower alicyclic alcohol of 1–12 carbon atoms. As concrete examples of the hydroxyl group-containing compound of this kind, various alcohols such as methanol, ethanol, propanol, isopropanol, n-butanol, isobutanol, sec-butanol, t-butanol, 1-pentanol, 2-pentanol, 3-pentanol, cyclopentanol, 1-hexanol, 2-hexanol, 3-hexanol, cyclohexanol, 1-heptanol, 2-heptanol, 3-heptanol, 1-octanol, isooctanol, 2-ethylhexanol, isononyl alcohol, and lauryl alcohol may be cited. These alcohols may be in a linear form or a branched form. They do not need to be used singly but may be used in the form of a combination of two or more members.

The easily polymerizing substance-containing solution is allowed to contain a mixture of a high boiling substance, a solvent, and a by-product occurring during the formation of the easily polymerizing substance in addition to the easily polymerizing substance. In the case of acrylic acid and acrylic esters, for example, the mixture of acetic acid, propionic acid, acrolein, maleic acid, water, and formalin which is by-produced during the formation of acrylic acid by the reaction of catalytic gas phase oxidation may be cited. Then, in the case of methacrylic acid and methacrylic esters, for example, the mixture of methacrolein, acrylic acid, and acetic acid which is by-produced during the formation of methacrylic acid by the reaction of catalytic gas phase oxidation may be cited.

Figure 5:
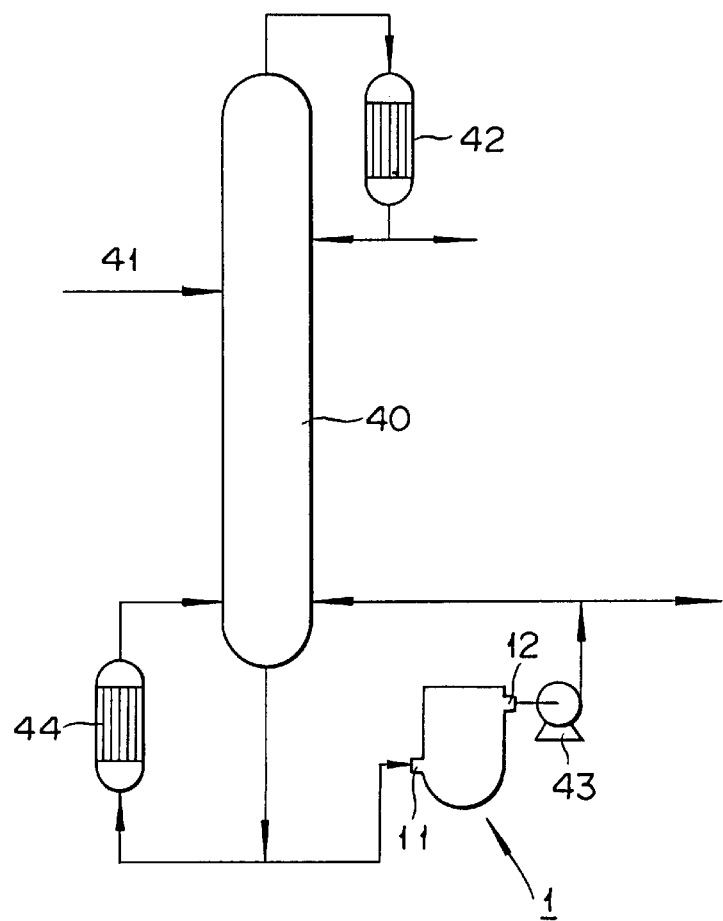
FIG. 5 is a horizontal cross section illustrating a purification apparatus of this invention having a purifying column and a solid substance removing device disposed therein.

The purifying apparatus and the method for the removal of the solid substance contemplated by this invention will be explained below with the aid of FIG. 5. With reference to FIG. 5, 1 represents the solid substance removing device, the fluid inlet pipe, 12 the fluid outlet pipe, 40 apurifying column, 41 a raw material supplying pipe, 42 a condenser, 43 a pump, and 44 a reboiler.

The purifying column (40) in the purifying apparatus of this invention, in spite of the designation, embraces all types of purifying apparatus which are generally used in the process of distillation and purification. Specifically, such contrivances as a distilling column, stripping column, absorbing column, rectifying column, separating column, extracting column, and collecting column which are used for the purification of a substance are embraced by this term. Among other columns enumerated above, the distilling column and the rectifying column prove particularly favorable. Further, in the treatment of distillation, absorption, and rectification, the easily polymerizing substance is frequently exposed to comparatively high temperatures. During this exposure, the accumulation of solid substance tends to occur inside the column, particularly on the bottom side of the column on account of such phenomena as polymerization and scorching. Particularly the distilling column and the rectifying column possess such parts as the reboiler on the column bottom side which tend to induce such phenomena as polymerization and scorching and, therefore, are most liable to entail accumulation of the solid substance. The use of the purifying apparatus of this invention permits these columns to be stably operated.

The place for installing the solid substance removing device (1) does not need to be limited particularly but is only required to fall on the circulating path in which the fluid under treatment in the purifying column (40) flows. This circulating path may be part of the pipe for passing the bottom liquid of the purifying column (40) or may be a pipe disposed separately. The solid substance removing device (1), therefore, may be connected to the circulating path which is used for advancing the fluid under treatment to the reboiler attached to the purifying column (40).

In this invention, since the bottom liquid of the purifying column (40) copiously contains such solid substance as a polymer, it is commendable to connect part of the pipe for the bottom liquid of the column and the fluid inlet pipe (11) of the solid substance removing device (1) in such a manner that the solid substance contained in the bottom liquid of the column will be infallibly removed. The fluid outlet pipe (12) may be connected to the pipe or the relevant device at the subsequent step in the purification of the easily polymerizing substance. It may be otherwise connected in such a manner that the fluid remaining after the removal of the solid substance will be circulated to the bottom part of the purifying column (40). Since the fluid thus circulated to the bottom part of the purifying column (40) is capable of removing the solid substance contained in the bottom liquid of the column, it serves the purpose of preventing the interior of the purifying column (40) from being blocked and enabling the purifying column to be operated stably.

In this case, at the bottom of the purifying column incorporated in the solid substance removing device (1), the linear velocity of the fluid of the body is generally in the range of 0.001–5 m/s, preferably in the range of 0.002–2.5 m/s, and more preferably in the range of 0.005–1 m/s. If this linear velocity falls short of 0.001m/s, the shortage will be at a disadvantage in slowing the treatment of the solid substance and enlarging the equipment and adding to the cost of equipment. Conversely, if the linear velocity exceeds 5 m/s, the excess will be at a disadvantage in lowering the ability of the device (1) to remove the solid substance. Though the introduction of the fluid to the fluid inlet pipe (11) is attained by the pressure of the inflow of the bottom liquid, the interposition of the pump (43) between the fluid outlet pipe (12) and the purifying column (40) permits smooth circulation of the fluid under treatment to the purifying column(40). In the purifying apparatus of this construction, the reboiler (44) and the condenser (42) may be additionally connected to the purifying column (40).

The fourth aspect of this invention consists in a method for the production of (meth)acrylic acid or an ester thereof by the use of the method for the removal of the solid substance mentioned above. When the method for the removal of the solid substance according to this invention is adopted, the production of an easily polymerizing substance can be carried out stably for a long time because the solid substance removing device (1) attached to the purifying column is capable of preventing the polymer of the easily polymerizing substance from accumulating in the purifying column (40) and, at the same time, preventing the polymer from being transferred to the subsequent step.

Figure 6:
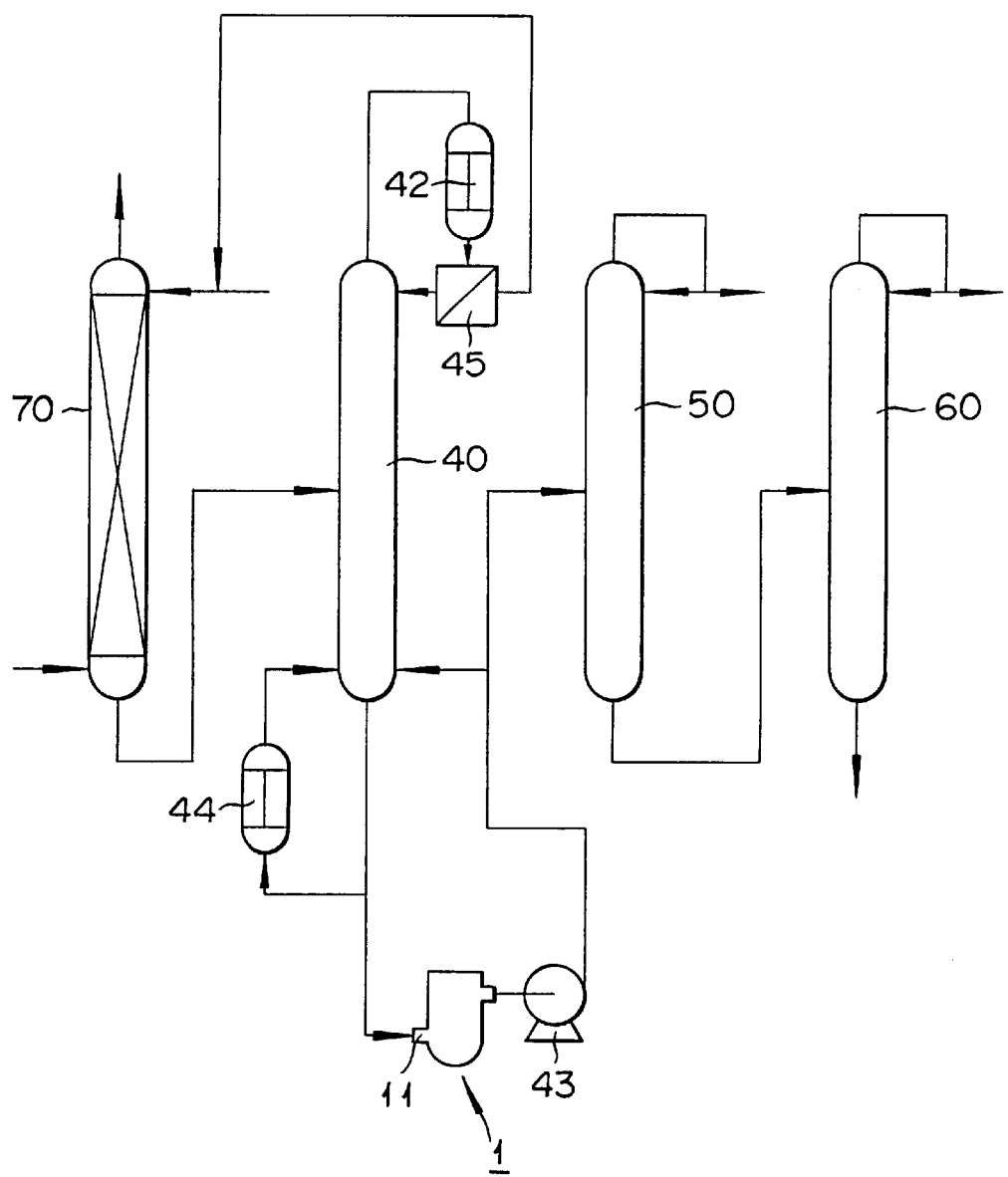
FIG. 6 is a process diagram portraying the production of acrylic acid by the use of the purifying apparatus of this invention.

Now, the application of the apparatus of this invention to the treatment of acrylic acid by distillation will be explained below with the aid of FIG. 6. With reference to FIG. 6, 1 represents the solid substance removing device, the fluid inlet pipe, 12 the fluid outlet pipe, 70 an acrylic acid absorbing column, 40 the purifying column, 42 the condenser, 43 the pump, 44 the reboiler, 45 a tank, 50 a light boiling point substance separating column, and 60 a high boiling point substance separating column.

In the absorbing column (70), generally an acrylic acid-containing gas is exposed to a water type absorbing agent which serves the purpose of absorbing the acrylic acid. As the conditions for the absorption in the absorbing column (70), the conditions heretofore known to the art may be adopted. This acrylic acid-containing solution is supplied from the bottom of the absorbing column (70) to the purifying column (40) and subjected in the purifying column (40) to a treatment for azeotropic dehydration.

In the purifying column (40), the acrylic acid-containing fluid, after adding an azeotropic solvent introduced via the top of the column, is heated and the gas expelled by evaporation from the top of the column is condensed in the condenser (42) and supplied as a reflux liquid via the tank (45) and dehydrated meanwhile. As the conditions for this azeotropic dehydration, the conditions used in the method heretofore known may be adopted. Optionally, part of the reflux liquid may be used as the absorbent in the absorbing column (70). The reflux liquid contains water, a solvent, and further acrylic acid and can be utilized to advantage. In consequence of this treatment of azeotropic dehydration, the acrylic acid-containing solution which has the water content lowered is collected in the bottom part of the purifying column (40).

The purifying column (40) is provided in the lower part thereof with the reboiler (44). The purifying column (40) and the reboiler (44) are interconnected through the medium of the pipe laid in the bottom part of the column for circulation therebetween. The pipe laid in the bottom part of the column is branched and connected to the fluid inlet pipe (11) of the solid substance removing device (1). The bottom liquid of the column which has been extracted via the extraction port disposed in the bottom of the purifying column (40) enters the reboiler (44) and the solid substance removing device (1), heated in the reboiler (44), the circulated to the purifying column (40) and deprived of the solid substance in the solid substance removing device (1), and then circulated forcibly by the subsequent pump (43) to the purifying column (40). As a result, the fluid under treatment in the purifying column (40) is prevented from stagnating and accumulating in the solid substance impurity removing device and the problem of adhesion of the solid substance impurity to the wall of the purifying column (40) is eliminated. The fact that the solid substance impurity is not accumulated in the fluid under treatment in the purifying column (40) immediately means that the solid substance impurity cannot adhere to the reboiler (44) and to the pipes laid in the vicinity thereof. Incidentally, the pipe for circulating the fluid from the pump (43) through the purifying column (40) is branched and connected to the light boiling point substance separating column (50). Consequently, the bottom liquid of the purifying column (40), after being deprived of the solid substance, is used as the liquid feed stock for the light boiling point substance separating column (50).

Then, in the bottom liquid which has the light boiling point substance separated therefrom in the light boiling point substance separating column (50), acrylic acid is contained in a concentrated state in conjunction with the high boiling point substance. The bottom liquid of the light boiling point substance separating column (50), therefore, is supplied to the high boiling point substance separating column (60) for the purpose of being deprived of the high boiling point substance. As the conditions for the separation of the light boiling point substance in the light boiling point substance separating column (50) and the conditions for the separation of the high boiling point substance in the high boiling point substance separating column (60), the conditions heretofore known to the art may be adopted. The light boiling point substance separating column (50) and the high boiling point substance separating column (60) may be provided in their bottom parts each with the solid substance impurity removing device (1) in the same manner as in the purifying column (40).

In the method for the production of (meth)acrylic acid or an ester thereof according to this invention, the occurrence of a polymer can be repressed by using a polymerization inhibitor for an easily polymerizing substance in such distilling columns as the absorbing column (70), the purifying column (40), the light boiling point substance separating column (50), and the high boiling point substance separating column(60). Thepolymerizationinhibitorswhichcanbeused in this case include at least one member selected from the group consisting of hydroquinone, methoxyhydroquinone, hydroquinone monomethyl ether, cresol, phenol, t-butyl catechol, diphenyl amine, phenothiazine, and methylene blue, at least one member selected from the group consisting of copper salt compounds such as copper dimethyldithiocarbamate, copper diethyldithiocarbamate, copper dibutyldithiocarbamate, and copper salicylate and manganese salt compounds such as manganese acetate, p-phenylenediamines such as p-phenylenediamine, N-oxyl compounds such as 4-hydroxy-2,2,6,6-tetramethyl-piperidineoxyl, ureas such as urea, and thioureas such as thiourea, for example. The compounds enumerated above may be used either singly or in the form of a combination of two or more members.

By feeding the fluid under treatment with a molecular oxygen-containing gas in addition to the polymerization inhibitor, it is made possible to perform the treatment in the purifying column stably over a longer time. The molecular oxygen-containing gas may be supplied to the fluid under treatment at any position in the path for the flow of the fluid. As concrete examples of the position for this supply, the piping system preceding the introduction into the purifying column, the bottom or the lateral side of the purifying column, the devices such as the reboiler attached to the purifying column, the pipes, the impurity removing part and the pipes laid adjacently thereto, and the path for the extraction of the residual liquid may be cited.

The amount of the molecular oxygen-containing gas to be introduced can be properly set to suit the purpose of use of the gas. In the distilling column for acrylic acid, for example, the amount of the gas is preferred to be in the range of 0.01–5.0 vol. %, based on the vapor flow rate of acrylic acid or an ester thereof expelled by evaporation.

Incidentally, the production of methacrylic acid can be attained by using methacrylic acid gas in the place of acrylic acid gas. The ester of this acid can be produced by causing the acid to react with a relevant alcohol.

EXAMPLES

Now, this invention will be more specifically described below by adducing working examples thereof.

Example 1

A purifying column of the construction of FIG. 5, measuring 1500 mm in inside diameter and having mounted therein 50 stepped sieve trays made of stainless steel (SUS316) was used. The column was provided in the top part thereof with an extraction port and a reflux liquid inlet pipe, in the central part thereof with an inlet pipe for the supply of the fluid as a raw material, in the bottom part thereof with a circulating pipe for the circulation of the fluid, and in the part halfway along the height of the column with a solid impurity removing device and a fluid delivery pump. The column was attached to the bottom part therewith a reboiler (vertical shell-and-tube type) in which the fluid passes the tube side in the form of natural circulation.

The solid impurity removing device had a laminated wire gauze having a thickness of 200 mm, a percentage of voids of 97.2%, and a contact surface area of 933 $m^2/m^3$ (diameter of wire in the wire gauze 0.12 mm and mesh size of 0.304 mm).

The liquid for the raw material was composed of 70 wt % of acrylic acid, 20 wt % of water, and 10 wt % of acetic acid. It was supplied through the 20th step of a distilling column at a flow rate of 2500 kg/h. As the reflux liquid, methyl isobutyl ketone was used. The operation of distillation was performed under a column top pressure of 150 hPa at a column bottom temperature of 100° C. to separate water and methyl isobutyl ketone from the top of the column and crude acrylic acid was recovered through the bottom of the column. The vapor flow rate of acrylic acid generated by distillation in the distilling column was set at about 7000 kg/hr, the ratio of reflux, R/D, at 5, the concentrating ration, F/B, at 1.5 (reflux liquid 4167 kg/h, distillation liquid 833 kg/h, and liquid extracted through the bottom of the column 1667 kg/h). Further, as the polymerization inhibitor, phenothiazine dissolved in the reflux liquid at a concentration of 200 ppm (amount relative to the vapor flow rate of acrylic acid generated by distillation) was introduced into the fluid. To the reboiler, a gas containing molecular oxygen at a ratio of 0.3 vol. % (the amount relative to the vapor flow rate of acrylic acid) was introduced through the lower part thereof. The amount of the fluid circulated in the bottom of the column was set at 1000 kg/h.

When the operation of the purifying column was continued for 10 days, the column always retained a stable condition without showing any abnormal change in the inner temperature of the column and the inner pressure of the column. When the operation was stopped and the interior of the column was visually inspected, no discernible adhesion of solid substance was detected in the interior of the column, the pipe for extraction of the bottom liquid of the column, the liquid delivering pump, or the reboiler. In the solid impurity removing device, 5 kg of a polymer was detected. This solid substance was removed by the cleaning operation performed in the solid substance removing device. The results are shown in Table 1. As used in Table 1, ⊙ denotes a column which was cable of operating continuously for not less than 10 days without incurring any problem, ○ denotes a column which was capable of operating continuously for not less than 10 days without inducing the reboiler to incur clogging in spite of a fluctuation in the temperature/pressure in the interior of the column, A denotes a column which was capable of operating continuously for not less than 6 days and incapable of preventing the reboiler from being clogged, and × denotes a column which was incapable of either operating continuously for not less than 5 days or preventing the reboiler from being clogged.

Example 2

In the purifying column of Example 1, a laminated wire gauze (diameter of wire in the gauze 0.12 mm and mesh size of 0.845 mm) having a thickness of 5 mm, a percentage of voids of 97.2%, and a contact surface area of 933 $m^2/m^3$ was used as the solid impurity removing device. When this purifying column was continuously operated for 10 days, it obtained a substantially stable state in spite of a slight fluctuation in the temperature and the pressure of the interior of the column. When the operation of the column was stopped and the interior of the column was visually inspected, about 1 kg of a deposit was detected in the column and certain amounts of the deposit were detected in the discharge pipe and the fluid transfer pump both emanating from the bottom of the column. No sign of adhesion of solid substance to the reboiler was detected. In the solid impurity removing device, 2 kg of a polymer was detected. This polymer was removed by performing a cleaning operation on the solid substance removing device. The results are shown in Table 1.

Example 3

In the purifying column of Example 1, a laminated wire gauze (diameter of wire in the gauze 0.12 mm and mesh size of 0.304 mm) having a thickness of 500 mm, a percentage of voids of 97.2%, and a contact surface area of 933 $m^2/m^3$ was used as the solid impurity removing device. When this purifying column was continuously operated for 10 days, it obtained a substantially stable state in spite of a fluctuation in the temperature and the pressure of the interior of the column and a slight fluctuation in the discharge pressure of the pump. When the operation of the column was stopped and the interior of the column was visually inspected, no sign of adhesion of solid substance was detected in the interior of the column, the discharge pipe emanating from the bottom of the column, the fluid delivery pump, or the reboiler. In the solid impurity removing device, 10 kg of a polymer was detected. This polymer was removed by performing a cleaning operation on the solid substance removing device. The results are shown in Table 1.

Example 4

In the purifying column of Example 1, a laminated wire gauze (diameter of wire in the gauze 0.20 mm and mesh size of 5.7 mm) having a thickness of 5 mm, a percentage of voids of 99.5%, and a contact surface area of 100 $m^2/m^3$ was used as the solid impurity removing device. When this purifying column was continuously operated for 10 days, the internal temperature of the column and the internal pressure of the column tended to increase slightly. The same phenomenon occurred in the apparatus of the subsequent step. When the operation of the column was stopped and the interior of the column was visually inspected, about 1 kg of a deposit was detected in the column and about 2 kg of the deposit was detected in the discharge pipe emanating from the bottom of the column and the fluid delivery pump. In the reboiler, 3 out of a total of 300 tubes were found in a clogged state. In the solid impurity removing device, 2 kg of a polymer was detected. This polymer was removed by performing a cleaning operation on the solid substance removing device. The results are shown in Table 1.

Example 5

In the purifying column of Example 1, a laminated wire gauze (diameter of wire in the gauze 2.66 mm and mesh size of 31.5 mm) having a thickness of 5 mm, a percentage of voids of 60%, and a contact surface area of 600 $m^2/m^3$ was used as the solid impurity removing device. When this purifying column was continuously operated for 10 days, the internal temperature of the column and the internal pressure of the column tended to increase slightly. The same phenomenon occurred in the apparatus of the subsequent step. When the operation of the column was stopped and the interior of the column was visually inspected, about 2 kg of a deposit was detected in the column and about 2 kg of the deposit was detected in the discharge pipe emanating from the bottom of the column and the fluid delivery pump. In the reboiler, 5 out of a total of 300 tubes were found in a clogged state. In the solid impurity removing device, 2 kg of a polymer was detected. This polymer was removed by performing a cleaning operation on the solid substance removing device. The results are shown in Table 1.

Example 6

In the purifying column of Example 1, a laminated wire gauze (diameter of wire in the gauze 0.01 mm and mesh size of 0.024 mm) having a thickness of 5 mm, a percentage of voids of 99.5%, and a contact surface area of 2000 $m^2/m^3$ was used as the solid impurity removing device. When this purifying column was continuously operated for 6 days, the internal temperature of the column and the internal pressure of the column were observed to fluctuate and the discharge pressure of the pump was observed to fluctuate. When the operation of the column was stopped and the interior of the column was visually inspected, about 2 kg of a deposit was detected in the column and about 2 kg of the deposit was detected in the discharge pipe and the fluid delivery pump both emanating from the bottom of the column. In the reboiler, 5 out of a total of 300 tubes were found in a clogged state. In the solid impurity removing device, 4 kg of a polymer was detected. This polymer was removed by performing a cleaning operation on the solid substance removing device. The results are shown in Table 1.

Comparative Example 1

In the purifying column of Example 1, a laminated wire gauze (diameter of wire in the gauze 1.3 mm and mesh size of 3.14 mm) having a thickness of 5 mm, a percentage of voids of 35%, and a contact surface area of 2000 $m^2/m^3$ was used as the solid impurity removing device. When this purifying column was operated for about 3 days, the mounted wire gauze showed an increase in the magnitude of AP, the column generated cavitation, and the pump stopped. The inner temperature and the inner pressure of the column were observed to fluctuate and the discharge pressure of the pump was observed to fluctuate. When the interior of the column was visually inspected, about 5 kg of a deposit was detected in the column and about 2 kg of the deposit was detected in the discharge pipe and the fluid delivery pump both emanating from the bottom of the column. In the reboiler, 5 out of a total of 300 tubes were found in a clogged state. In the solid impurity removing device, 4 kg of a polymer was detected. This polymer was removed by performing a cleaning operation on the solid substance removing device. The impeller was observed to have sustained damage due to the occurrence of cavitation. The results are shown in Table 1.

Comparative Example 2

In the purifying column of Example 1, a laminated wire gauze (diameter of wire in the gauze 0.4 mm and mesh size of 63.4 mm) having a thickness of 5 mm, a percentage of voids of 99.5%, and a contact surface area of 50 $m^2/m^3$ was used as the solid impurity removing device. When this purifying column was operated for about 3 days, the fluctuation of the discharge pressure of the pump induced generation of cavitation and brought the pump to a stop. The inner temperature and the inner pressure of the column were also observed to fluctuate. The same phenomenon occurred in the apparatus of the subsequent step. When the interior of the column was visually inspected, about 4 kg of a deposit was detected in the column and about 4 kg of the deposit was detected in the discharge pipe emanating from the bottom of the column and the fluid delivery pump. In the reboiler, 10 out of a total of 300 tubes were found in a clogged state. In the solid impurity removing device, 1 kg of a polymer was detected. This polymer was removed by performing a cleaning operation on the solid substance removing device. The results are shown in Table 1.

Comparative Example 3

In the purifying column of Example 1, a 60-mesh equivalent strainer (diameter of wire 0.17 mm and mesh size of 0.3 mm) having a thickness of 0.16 mm, a percentage of voids of 35%, and a contact surface area of 15000 $m^2/m^3$ was used as the solid impurity removing device. When this purifying column was operated for about 3 days, the fluctuation of the discharge pressure of the pump induced generation of cavitation and brought the pump to a stop. The inner temperature and the inner pressure of the column were also observed to fluctuate. When the interior of the column was visually inspected, about 5 kg of a deposit was detected in the column and about 2 kg of the deposit was detected in the discharge pipe emanating from the bottom of the column and the fluid delivery pump. In the reboiler, 10 out of a total of 300 tubes were found in a clogged state. In there boiler, a large amount of a polymer was detected. This polymer was removed by performing a cleaning operation on the distilling column, the reboiler, the strainer, etc. This operation consumes a large amount of a detergent solvent and a great deal of time. The strainer, during the cleaning operation, emitted offensive odor. The results are shown in Table 1.

Comparative Example 4

In the purifying column of Example 1, a 10-mesh equivalent strainer (diameter of wire 0.71 mm and mesh size of 1.78 mm) having a thickness of 0.7 mm, a percentage of voids of 50%, and a contact surface area of 2800 $m^2/m^3$ was used as the solid impurity removing device. When this purifying column was operated for about 3 days, the fluctuation of the discharge pressure of the pump induced generation of cavitation and brought the pump to a stop. The inner temperature and the inner pressure of the column were also observed to fluctuate. The same phenomenon occurred in the apparatus of the subsequent step. When the interior of the column was visually inspected, about 5 kg of a deposit was detected in the column and about 2 kg of the deposit was detected in the discharge pipe emanating from the bottom of the column and the fluid delivery pump. In the reboiler, 10 out of a total of 300 tubes were found in a clogged state. In the reboiler, a large amount of a polymer was detected. This polymer was removed by performing a cleaning operation on the distilling column, the reboiler, the strainer, etc. This operation consumed a large amount of a detergent solvent and a great deal of time. The impeller was observed to have sustained damage due to the generation of the cavitation. The strainer, during the cleaning operation, emitted offensive odor. The results are shown in Table 1.

Comparative Example 5

In the purifying column of Example 1, a strainer (diameter of wire 1 mm and mesh size of 98.5 mm) having a thickness of 1 mm, a percentage of voids of 98%, and a contact surface area of 80 $m^2/m^3$ was used as the solid impurity removing device. When this purifying column was operated for about one hour, the fluctuation of the discharge pressure of the pump induced generation of cavitation and brought the pump to a stop. The inner temperature and the inner pressure of the column were also observed to fluctuate. The same phenomenon occurred in the apparatus of the subsequent step. When the interior of the column was visually inspected, about 5 kg of a deposit was detected in the column and a large amount of the deposit was detected in the discharge pipe emanating from the bottom of the column and the fluid delivery pump. In the reboiler, one out of a total of 300 tubes was found in a clogged state. In the strainer, a large amount of a polymer was detected. This polymer was removed by performing a cleaning operation on the distilling column, the reboiler, the strainer, etc. This operation consumed a large amount of a detergent solvent and a great deal of time. The impeller was observed to have sustained damage due to the generation of the cavitation. The strainer, during the cleaning operation, emitted offensive odor. The results are shown in Table 1.

TABLE 1

|  | Example 1 | Example 2 | Example 3 | Example 4 | Example 5 | Example 6 | Example 1 | Example 2 | Example 3 | Example 4 | Example 5 |
|---|---|---|---|---|---|---|---|---|---|---|---|
| solid substance removing device | | | | | | | | | | | |
| Type | Wire gauze | | | | | | Wire gauze | | 60-mesh strainer | 10-mesh strainer | ordered strainer |
| Thickness: H (mm) | 200 | 5 | 500 | 5 | 5 | 5 | 5 | 5 | 0.16 | 0.7 | 1 |
| Percentage of voids: $\epsilon$ (%) | 97.2 | 97.2 | 97.2 | 99.5 | 60 | 99.5 | 35 | 99.5 | 35 | 50 | 98 |
| Contact surface area: b (m$^2$/m$^3$) | 933 | 933 | 933 | 100 | 600 | 2000 | 2000 | 50 | 15000 | 2800 | 80 |
| body diameter (mm) | 600 | 600 | 600 | 600 | 600 | 600 | 600 | 600 | — | — | — |
| V (m$^3$)*1 | 5.65E−02 | 1.413E−03 | 1.413E−01 | 1.413E−03 | 1.413E−03 | 1.413E−03 | 1.413E−03 | 1.413E−03 | 1.413E−03 | 1.413E−03 | 1.413E−03 |
| V$_1$ (m$^3$)*2 | 1.583E−03 | 3.956E−05 | 3.956E−03 | 7.065E−06 | 5.652E−04 | 7065E−06 | 9.185E−04 | 7.065E−06 | 9.185E−04 | 7.065E−04 | 2.826E−05 |
| V$_2$ (m$^3$)*3 | 5.49E−02 | 1.373E−03 | 1.373E−01 | 1.406E−03 | 8.478E−04 | 1.406E−03 | 4.946E−04 | 1.406E−03 | 4.946E−04 | 7.065E−04 | 1.385E−03 |
| wire diameter (mm) | 0.120 | 0.120 | 0.120 | 0.200 | 2.667 | 0.010 | 1.300 | 0.400 | 0.173 | 0.714 | 1.000 |
| P$_t$ (mm)*4 | 0.424 | 0.965 | 0.424 | 15.899 | 34.168 | 0.034 | 4.438 | 63.799 | 0.472 | 2.499 | 99.497 |
| Mesh ρ (mm) | 0.304 | 0.845 | 0.304 | 15.699 | 31.501 | 0.024 | 3.138 | 63.399 | 0.298 | 1.784 | 98.497 |
| N (Number/mm)*5 | 0.48 | 1 | 0.48 | 1 | 1 | 1 | 1 | 1 | | | |
| W$_1$ (m$^3$)*6 | 3.392E−05 | 3.392E−05 | 3.392E−05 | 5.652E−05 | 7.536E−04 | 2.826E−06 | 3.674E−04 | 1.130E−04 | 1.531E−03 | 1.442E−03 | 1.413E−03 |
| M (piece)*7 | 96 | 5 | 240 | 5 | 5 | 5 | 5 | 5 | 1 | 1 | 1 |
| K*8 | 0.4859 | 0.2333 | 0.4859 | 0.0250 | 0.1500 | 0.5000 | 0.5000 | 0.0125 | 0.6000 | 0.4900 | 0.0200 |
| State of operation | continued | | | | | | | | stopped | | |
| operated days | 10 days | 10 days | 10 days | 10 days | 10 days | 6 days | 3 days | 3 days | 3 days | 3 days | 1 hr |
| Cavitation | none | none | slight | none | none | generated | | | generated | | |
| Fluctuation of temp. and press. | none | | occurred in temp. & press. | | | | | | occurred in temp. & press. | | |
| Influence to subsequent step | none | none | none | occurred | occurred | occurred | occurred | occurred | occurred | occurred | occurred |
| generation of solid substance | | | | | | | | | | | |
| Removing device pipe | 5 kg | 2 kg | 10 kg | 2 kg | 2 kg | 4 kg | 4 kg | 1 kg | large | large | large |
| | none | slight | none | 2 kg | 2 kg | 2 kg | 2 kg | 4 kg | 2 kg | 2 kg | large |
| Interior of column | none | 1 kg | none | 1 kg | 2 kg | 2 kg | 5 kg | 4 kg | 5 kg | 5 kg | 5 kg |
| number of clogged tube in reboiler | none | none | none | 3 | 5 | 5 | 5 | 10 | 10 | 10 | 1 |
| Other | none | none | none | none | none | none | none | none | | difficult of washing | |
| Overall rating | ⊚ | ◯ | ◯ | Δ | Δ | Δ | X | X | X | X | X |

*1: V; total of the volume of the wire gauzes and the volume of the empty space part
*2: V$_1$; volume of the wire gauzes,
*3: V$_2$; volume of empty space,
*4: P$_t$; pitch of wire gauze,
*5: N; number of wire gauzes/thickness,
*6: W$_1$; volume of wire gauze/sheet,
*7: M; total number of wire gauzes,
*8: K; ratio of patching of wire gauze/sheet

What is claimed is:

1. A solid substance removing device comprising a body provided with a fluid inlet pipe and a fluid outlet pipe and a filtering part disposed between said fluid inlet pipe and said fluid outlet pipe inside said body, said filtering part having
   (a) a thickness in the range of 5–500 mm,
   (b) a percentage of voids in the range of 60–99.5 vol. %, and
   (c) a contact surface area in the range of 100–2000 m$^2$/m$^3$.

2. A device according to claim 1, wherein said body is provided therein with means for producing a swirling current of the fluid introduced through said fluid inlet pipe.

3. A device according to claim 1, wherein said means for producing the swirling current is obtained by at least one of the operations of disposing guide vanes in said fluid inlet pipe, disposing a baffle in said fluid inlet pipe, and/or, disposing said fluid inlet pipe at an angle in the range of 30–60° from the tangential line of said body where the body is in tubular shape.

4. A device according to claim 1, which is provided with a gas discharge preventing mechanism.

5. A device according to claim 4, wherein said gas discharge preventing mechanism is a baffle disposed in the proximity of the connecting part of said fluid outlet pipe inside said body or has a construction which said fluid outlet pipe is thrust into said body from outside and terminated toward the liquid level in said body.

6. A purifying apparatus which has disposed in a purifying column handling an easily polymerizing substance and provided with a solid substance removing device thereon set forth in any of claim 1.

* * * * *